(12) United States Patent
Nathoo

(10) Patent No.: US 7,833,539 B2
(45) Date of Patent: Nov. 16, 2010

(54) TOOTH WHITENING HYDROGELS

(75) Inventor: Salim A. Nathoo, Piscataway, NJ (US)

(73) Assignee: Oral Health Clinical Services, LLC, Piscataway, NJ (US)

( * ) Notice: Subject to any disclaimer, the term of this patent is extended or adjusted under 35 U.S.C. 154(b) by 0 days.

(21) Appl. No.: 10/861,914

(22) Filed: Jun. 7, 2004

(65) Prior Publication Data

US 2005/0019276 A1    Jan. 27, 2005

Related U.S. Application Data

(63) Continuation of application No. 09/920,674, filed on Aug. 2, 2001, now Pat. No. 6,746,679.

(51) Int. Cl.
*A61K 6/00* (2006.01)
*A61K 8/00* (2006.01)
*A61K 8/02* (2006.01)
*A61K 8/22* (2006.01)

(52) U.S. Cl. .......................... 424/401; 424/49; 424/52; 424/53; 424/601; 424/613; 433/215; 433/216; 433/217.1

(58) Field of Classification Search ................ 424/49, 424/53
See application file for complete search history.

(56) References Cited

U.S. PATENT DOCUMENTS

| | | | | |
|---|---|---|---|---|
| 4,097,604 A | * | 6/1978 | Thiele | 514/560 |
| 4,980,152 A | * | 12/1990 | Frazier et al. | 424/52 |
| 5,879,691 A | * | 3/1999 | Sagel et al. | 424/401 |
| 6,048,202 A | * | 4/2000 | Jensen et al. | 433/136 |
| 6,096,328 A | * | 8/2000 | Sagel et al. | 424/401 |
| 6,174,516 B1 | * | 1/2001 | Curtis et al. | 424/53 |
| 6,228,347 B1 | * | 5/2001 | Hersh | 424/49 |
| 6,343,932 B1 | * | 2/2002 | Wiesel | 433/215 |
| 6,719,995 B2 | * | 4/2004 | Rajaiah et al. | 424/435 |

FOREIGN PATENT DOCUMENTS

WO    WO 99/62472    * 12/1999

* cited by examiner

*Primary Examiner*—Frederick Krass
*Assistant Examiner*—Lezah W Roberts
(74) *Attorney, Agent, or Firm*—Townsend and Townsend and Crew LLP

(57) ABSTRACT

This invention relates generally to compositions for whitening human teeth, and more particularly, to compositions that do not contain hydrocarbon humectants and which, when applied onto the surface of teeth act to whiten without damage to tooth surfaces. They do contain a hydrogel, defined as a gel that does not contain a hydrocarbon humectant. A hydrocarbon humectant is defined as a carbon, hydrogen and oxygen compound which is used to prevent the oral care composition from hardening upon exposure to air or a carbon, hydrogen and oxygen compound which is used as a carrier for ingredients of an oral care composition. The tooth whitening of the present invention is free of a humectant and contains a peroxide, in combination with a mixed surfactant system, a mixed metal chelating system of a peptilytic condensed pyrophosphate chelating agent, an organic chelating agent, and a metal precipitating chelating agent, a catalase inhibiting compound and a non-ionic polyoxyethylene polyoxypropylene block copolymers surfactant thickening agent as hereinafter defined. As will be illustrated, the oral compositions of the present invention are in the form of gels that exhibit better whitening effect, do not cause dental hypersensitivity and can be used both in the dental office and in-home brushing or splint applications.

15 Claims, No Drawings

TOOTH WHITENING HYDROGELS

This application is a continuation of U.S. patent application Ser. No. 09/920,674, filed on Aug. 2, 2001 now U.S. Pat. No. 6,746,679, which is expressly incorporated fully herein by reference.

BACKGROUND OF THE INVENTION

1. Field of the Invention

This invention relates generally to compositions for whitening human teeth, and more particularly, to compositions that do not contain hydrocarbon humectants and which when applied onto the surface of teeth act to whiten without damage to tooth surfaces.

2. The Prior Art

A tooth is comprised of an inner dentin layer and an outer hard enamel layer which is coated with a protective layer called the pellicle. Teeth can become stained when the chromogenic materials penetrate the enamel or chromogenic materials get trapped within the pellicle.

Many substances can stain or reduce the whiteness of one's teeth. In particular, the foods, tobacco products and fluids such as tea and coffee that one consumes tend to stain one's teeth. These products or substances tend to accumulate within the pellicle and then permeate the enamel. This problem occurs gradually over many years, but imparts a noticeable discoloration of the enamel of one's teeth.

Stain can be removed from tooth surfaces by the use of dentifrices, especially toothpaste, gels and powders containing active oxygen or hydrogen peroxide liberating ingredients such as peroxides, percarbonates and perborates of alkali and alkaline earth metals or complex compounds containing hydrogen peroxide with salts of the alkali or alkaline earth metals. However, these methods generally work very slowly and do not fulfill the needs of individuals who desire rapid whitening of teeth.

Individuals desiring rapid whitening of teeth can usually have it done in the dental office. One method for whitening teeth used by dental professionals involves the use of 30-35% hydrogen peroxide in combination with heat and/or light to promote the oxidation reaction. This method, although fast, is losing favor with dentists because clinical and scientific evidence shows that high concentrations of peroxide are deleterious to oral tissues. Improvements to this method have resulted in the usage of lower concentrations of hydrogen peroxide. However, this method also has a drawback because it is expensive and confines the patient to the dental chair for extended periods of time.

Another professional method for bleaching teeth involves the use of hydrogen peroxide generating compounds such as urea peroxide (carbamide peroxide) at concentrations of 10-20% to achieve the desired whitening effect. Urea peroxide rapidly breaks down into hydrogen peroxide due to the water present in saliva. This method known as at home use dentist dispensed bleaching system involves the use of a mouth guard or tray within which the bleaching agent is placed. The tray is then placed upon the teeth of the patient and bleaching is allowed to take place. This method of treatment has drawbacks including tooth sensitivity, possibly due to demineralization and irritation of oral tissues. An additional disadvantage of the tray application method is that the bleaching effect is very slow compared to in-office methods.

One of the drawbacks to home use bleaching products containing oxygen liberating bleaching compounds is the tendency of these products to decompose within a relatively short period of time following manufacture with concomitant loss of all or a substantial amount of the available oxygen thereby limiting the efficacy of these products as teeth whitening compositions. Peroxy compounds such as hydrogen peroxide are notoriously unstable with respect to maintenance of peroxide level and have been found to be difficult to formulate into aqueous gels or pastes which will have an adequate shelf-life and yet will readily liberate oxygen when applied to the oral cavity. Therefore, the prior art, for example U.S. Pat. Nos. 4,988,450 and 3,657,413 in formulating oxygen liberating compositions for the whitening of teeth utilize anhydrous powders or water-free pastes or gels which must be protected against contamination and chemical interaction. A drawback to the use of such anhydrous products is that, due to the absence of water, application of the oral composition tends to desiccate oral tissues which leads to irritation and tissue damage.

In order to overcome the disadvantage of irritation and tissue desiccation, prior art discloses oxygen releasing toothpaste compositions which have greater water content, however all have hydrocarbon humectants or hydrocarbon carriers such as glycerin, sorbitol, polyethylene glycol etc. The purpose of the humectant is to keep the composition from hardening upon exposure to air. Illustrative of oral compositions containing peroxide compounds include U.S. Pat. Nos. 4,980,152; 4,839,156; 4,522,805; 4,567,036; 4,405,599; 4,980,152; 5,171,564; and 5,256,402.

U.S. Pat. No. 4,980,152 discloses a non-abrasive aqueous oral gel composition comprising about 0.5 to about 10% by weight urea peroxide and 0.01 to 2% by weight of a fluoride providing compound. The composition further includes a thickening agent such as carboxy polymethylene, a non-ionic surfactant such as Pluronic F127, alkali soluble cellulose ethers as viscosity increasing agents, potassium phosphate as a buffering agent and glycerin as a carrier and flavoring and sweetening agents.

U.S. Pat. No. 4,839,156 discloses an aqueous dental gel containing 18-25% by weight of a polyoxyethylene polypropylene block copolymer gelling agent, hydrogen peroxide, 15-40% by weight of a polyethylene glycol humectant, flavor, sweetening agent and a non-ionic surfactant as the essential ingredients. This has been defined as a ringing gel, however addition of metal chelating agents have been described to have an adverse impact upon the stability of peroxide.

U.S. Pat. Nos. 4,522,805 and 4,567,036 disclose a stable toothpaste to aid in controlling periodontal disease, containing an oxidizing agent such as urea peroxide which dissociates into urea and hydrogen peroxide in the oral cavity, in a paste carrier comprising an anionic detergent, sorbitol and glycerin humectant and a thickening agent such as gum tragacanth, sodium alginate or sodium carboxymethyl cellulose.

U.S. Pat. No. 4,405,599 discloses toothpaste consisting essentially of a combination of calcium peroxide and sodium perborate oxidizing agents, dicalcium phosphate, calcium carbonate and magnesium carbonate cleaning agents, sorbitol humectant, cornstarch, cellulose gum thickening agents, and an anionic detergent. There is no indication of the effect of the toothpaste on whitening or stain removal from teeth.

U.S. Pat. No. 4,980,152 discloses toothpaste consisting of urea or hydrogen peroxide with a fluoride compound as a pH stabilizing compound. There is no indication of the effect of the toothpaste on whitening or stain removal from teeth.

U.S. Pat. No. 5,171,564 discloses an oral care composition which contains an abrasive in combination with a metal free peroxide, a chelating agent, thickening agent such as a polyoxyethylene polypropylene block copolymer and humectants such as polyethylene glycol, glycerin or sorbitol.

U.S. Pat. No. 5,256,402 discloses an oral care composition which contains an abrasive in combination with a metal free peroxide, a chelating agent, tooth desensitizing agents and thickening agent such as a polyoxyethylene polypropylene block copolymer and humectants such as polyethylene glycol, glycerin or sorbitol.

The prior art listed above, all contain hydrocarbon humectants and have a primary drawback of having limited stain removal/tooth whitening effectiveness. The purpose of the hydrocarbon humectants in tooth whitening compositions is to help solubilize flavor materials, surfactants and also to act as a carrier for peroxides. However, hydrocarbon humectants have a disadvantage because they are known to react with the active bleaching species such as free radicals and the perhydroxyl anions. Other prior art compositions contain abrasives which have been shown to abrade enamel. In addition, newer tooth colored restorative materials contain very fine filler particles in order to increase polishability unfortunately, this has been shown to decrease abrasion resistance. Hence, there is a need for toothbrush applied dentifrice compositions which do not contain hydrocarbon humectants and do not contain abrasives.

Dentist dispensed splint applied compositions are thought to have greater activity because the contact time between the tooth and the oxygen generating compound is increased via the use of a splint or a mouth tray. Illustrative examples of the tray-applied tooth whitening systems include U.S. Pat. Nos. 5,376,006; 5,858,332; 5,764,598; 5,718,886 and 5,171,564

U.S. Pat. No. 5,376,006 discloses splint applied sustained release oral care compositions, which contain a peroxide, a carbomer thickening agent, water and glycerin as a humectant/carrier. These compositions are claimed to be sustained release and require the splint to be worn for greater then two hours.

U.S. Pat. No. 5,858,332 discloses sustained release splint applied oral care compositions which contain a peroxide, a carbomer thickening agent, water, a carboxylic acid peroxide stabilizer and glycerin as a humectant/carrier. These compositions are claimed to be sustained release and require the splint to be worn for greater then two hours.

U.S. Pat. No. 5,746,598 discloses sustained release splint applied oral care compositions which contain a peroxide, a carbomer thickening agent, water, sodium fluoride and glycerin/polyethylene glycol as a humectant/carrier. These compositions are claimed to be sustained release and require the splint to be worn for greater then two hours.

U.S. Pat. No. 5,718,886 discloses splint applied oral care compositions which contain a peroxide, a thickening system consisting of carboxypolymethylene, hydroxypropyl cellulose and xanthan gum. The carriers/humectants are propyleneglycol, polyethyleneglycol, and glycerin.

The drawback with the splint applied compositions described above is that all contain hydrocarbon humectants which may limit the activity of the peroxide ingredient and none contain surface active agents whose absence may prevent solubilization and emulsification of the stain and thus may lead to redeposition of the stain thereby further limiting the bleaching effectiveness of the peroxide.

In contrast to the above, U.S. Pat. No. 5,171,564 discloses an oral care composition which contains an abrasive in combination with a metal free peroxide, a chelating agent, thickening agent such as a polyoxyethylene polypropylene block copolymer and hydrocarbon humectants such as polyethylene glycol, glycerin or sorbitol. This composition is claimed to have utility in brushing applications and splint applied tooth bleaching applications. As in the case above, this composition has a drawback because it contains a hydrocarbon humectant.

Prior art also discloses bleaching gels e.g., U.S. Pat. No. 5,922,307 in which the water content is increased to at least 75% in order to reduce tooth sensitivity and other adverse effects such as demineralization. This patent also teaches the utility of using a calcium chelating agent in order to stabilize the peroxide and enhance the whitening effect. Unfortunately, chelating agents have been shown to increase enamel demineralization in absence of a calcium precipitating agent such as sodium fluoride.

Prior art related to tooth whitening does not mention the possibility of increasing the tooth whitening efficacy by inhibiting the action of catalase. Catalase is an enzyme which has been shown to occur naturally in plague and in saliva. The primary role of catalase is to breakdown hydrogen peroxide into oxygen and water which have a very limited effect on bleaching teeth. Hence, limiting catalase activity would increase the bleaching effect of the peroxide. Prior art concerning bleaching of cellulose paper fibers (U.S. Pat. No. 5,885,412) addresses the issue of premature breakdown and teaches that catalase inhibitors prevent breakdown of peroxide, thus requiring less peroxide for bleaching purposes. The inhibitors of catalase include halogenated compounds such as sodium fluoride, sodium chloride, sodium bromide, hydroxylamine, sulfides and reducing agents such as ascorbic acid. Notably, the catalase inhibiting technology has not been utilized in oral care compositions in order to enhance tooth whitening efficacy.

As indicated above some compositions contain chelating agents. A metal chelating agent can be defined as an agent which sequesters metal ions and renders them unreactive. Generally, there are two types of metal chelating agents. These are: 1) agents such as EDTA, citric acid, alkali metal pyrophospates, phosphonates etc., which combine with metal ions and keep them in solution. These are further divided into two groups; a) organic chelating agents and b) inorganic chelating agents. 2) agents that react with metal ions and cause them to precipitate. An example of this includes fluorides such as sodium fluoride. In prior art concerning non-dental bleaching compositions, chelating agents which keep metal ions in solution have shown to be advantageous because they prevent metal catalyzed breakdown of peroxide. Further, U.S. Pat. No. 6,150,324 teaches the utility of using detergent additives in combination with a mixed metal sequestrant system to obtain improved dishware cleaning compositions. Tooth bleaching prior art does not disclose the benefit of using mixed organic metal chelating agents and condensed phosphate chelating agents in order to obtain compositions which have heightened tooth-whitening abilities. Tooth bleaching prior art also does not disclose the benefit of using metal precipitating chelating agents such as fluorides in order to stabilize the peroxide formulations and also to precipitate calcium compounds onto the tooth surface thus preventing enamel damage. Further, there is contradictory information concerning the utility of metal solubilizing chelating agents in stabilization of peroxide containing dental preparations. U.S. Pat. No. 4,839,156 teaches that chelating agents have adverse effects upon the stability of peroxides. In contrast, U.S. Pat. No. 5,171,564 teaches that chelating agents are essential to the stability of the peroxide preparation. The reason behind this discrepancy is unknown. However, the use of chelating agents that solubilize metal ions offer distinct disadvantages because studies have shown that these agents demineralize and damage enamel surfaces.

Tooth whitening products currently available have additional disadvantages in addition to being slow acting and having adverse effects. These include: poor compliance because compliance in a therapeutic regimen has been shown to be related to the length of the therapy and the frequency of the dosage.

Hence, there is a need for a bleaching product that is safe, rapidly acting and one that fits into the lifestyle of the patient.

SUMMARY OF THE INVENTION

In accordance with the present invention, a hydrogel is defined as a gel that does not contain a hydrocarbon humectant. A hydrocarbon humectant is defined as a carbon, hydrogen and oxygen compound which is used to prevent the oral care composition from hardening upon exposure to air; or a carbon, hydrogen and oxygen compound which is used as a carrier for ingredients of an oral care composition. The tooth whitening of the present invention is free of a humectant and contains a peroxide, in combination with a mixed surfactant system, a mixed metal chelating system consisting of peptilytic condensed pyrophosphate chelating agent, an organic chelating agent, and a metal precipitating chelating agent, a catalase inhibiting compound and a non ionic polyoxyethylene polyoxypropylene block copolymers surfactant thickening agent as hereinafter defined.

As will be illustrated, the oral compositions of the present invention are in the form of a gel that exhibits better whitening effect and does not cause dental hypersensitivity and can be used both in the dental office and in-home brushing or splint applications.

DETAILED DESCRIPTION OF THE INVENTION

The dentifrice compositions of the present invention are free of hydrocarbon humectants and are formulated using as the essential ingredients: water, a peroxide compound as the whitening agent, a mixed surfactant system consisting of an anionic surfactant such as sodium lauryl sulfate and non-ionic surfactant such as Tween 20, which is a polyoxyethylene (20) sorbitan monolaurate, a mixed metal chelating system which includes a condensed pyrophosphates e.g., sodium pyrophosphate, an organic chelating agent consisting of 1-hydroxy ethylidene 1,1-diphosphonoc acid and a metal precipitating agent such as sodium fluoride. The composition also contains inhibitors of catalase such as sodium fluoride. The thickening system consists of a non ionic polyoxyethylene polyoxypropylene block copolymers surfactant.

Examples of suitable peroxide compounds used to prepare the oral compositions of the present invention include hydrogen peroxide and organic peroxides including urea peroxide, glyceryl peroxide, benzoyl peroxide and the like. A preferred peroxide is hydrogen peroxide.

Typically, the peroxide compound can be employed in the composition of the present invention in amounts so that at least about 1% by weight of the composition comprises a peroxide. Preferably, the peroxide compound comprises from about 2 to about 30% by weight of the composition. More preferably, the peroxide comprises from about 3 to about 15% by weight of the composition. A typical peroxide concentration in the composition is generally about 2 to 7% by weight for home use products and about 15 to 20% for dental professional use.

Surfactants are also included in the dentifrice compositions of the present invention and serve as solubilizing, dispersing, emulsifying agents and agents that reduce the surface tension of the teeth in order to increase the contact between the tooth and the peroxide. The surfactants may also help solubilize, disperse and emulsify stain within the intercrystalline spaces thus further aiding the penetration of peroxide. The surfactant comprises about 0.05 to 5.0% by weight and preferably 0.1 to 4% by weight of the oral composition. The mixed surfactant system consists of about 1:1 w/w ratio of the anionic surfactant: non-ionic surfactant. Particularly useful surfactants include nonionic surfactants such as a water soluble polyoxyethylene monoester of sorbitol with a C.sub. 10-18 fatty acid ester of sorbitol (and sorbitol anhydrides), consisting predominantly of the monoester, condensed with about 10-30, preferably about 20, moles of ethyleneoxide. The fatty acid (aliphatic hydrocarbon-monocarboxylic acid) may be saturated or unsaturated, e.g. lauric, palmitic, stearic, oleic acids. Tween 20, which is a polyoxyethylene (20) sorbitan monolaurate is especially preferred.

Anionic surfactants such as water soluble salts of higher fatty acid monoglyceride monosulfates, such as sodium salts of the monosulfated monoglycerides, or hydrogenated coconut oil fatty acids, higher alkylsulfates, such as sodium lauryl sulfate and alkyl aryl sulfonates, such as sodium dodecyl benzene sulfonate. Sodium lauryl sulfate is especially preferred.

Other surfactants such as flouorinated surfactants and surface tension reducing materials may also be incorporated within the compositions.

Thickening or gelling agents used in the formulation of the dentifrice include nonionic polyoxyethylene polyoxypropylene block copolymers. Illustrative of polyoxyethylene polyoxypropylene block copolymers useful in the practice of the present invention include block copolymers having the formula $$HO(C_2CH_4O)_b(C_3H_6O_6)_a(C_2H_4O)_bH$$

wherein a is an integer such that the hydrophobic base represented by $(C_3H_6O_6)$ has a molecular weight of about 2750 to 4000, b is an integer such that the hydrophilic portion (moiety) represented by $(C_2H_4O)$ constitutes about 70-80% by weight of the copolymer. Block copolymers of this composition are available commercially under the trademark Pluronic F type.

Pluronic F127, which has a molecular weight of 4000 and contains 70% of the hydrophilic polyoxyethylene moiety is preferred in the practice of the present invention.

The thickening agents are preferably present in the dentifrice in an amount within the range of about 15 to about 50 percent by weight and about 25 to about 45 percent by weight is preferred for use in the compositions of the present invention.

Agents which chelate metal ions are an essential ingredient of the present invention. The chelating agents are comprised of a blend of chelating agents which include metal solubilizing agents and metal precipitating agents. The metal solubilizing agents include a condensed pyrophosphate compound. For purposes of this invention "condensed phosphate" relates to an inorganic phosphate composition containing two or more phosphate species in a linear or cyclic pyrophosphate form. The preferred condensed phosphate is sodium pyrophosphate but may also include tripolyphosphate, hexametaphosphate, cyclic condensed phosphate or other similar phosphates well known in the field. The blend also includes an organic chelating agent. The term "organic phosphate" includes phosphonic acid, di and tri phosphonoc acid compound or its salts. The preferred phosphonic acid is sold under the trade name of Dequest 2010 and is called 1-hydroxyethylidene-1,1-diphosphonic acid. The blend also includes a metal precipitating chelating agent. The term "metal precipitating chelating agent" is an agent that binds to metals and causes the metal to precipitate and includes halogens such as fluoride. The chelating agents are incorporated in the dentifrice compositions of the present invention in an amount within the range of 0.1 to about 8.0% by weight and preferably about 0.5 to about 3.0% by weight in a ratio of about 3:1:1 w/w organic chelating agent: condensed phosphate chelating agent: metal precipitating agent.

In prior art it has been proposed that chelating agents stabilize the oxygen generating compound and increase the whitening effectiveness by removing the blockage of intercrystalline spaces thus enhancing the penetration of peroxide into the tooth. The removal of the precipitate from the intercrystalline spaces may have a negative effect upon the safety of peroxide mediated tooth whitening because studies have shown that unblocking spaces may lead to adverse effects such a increased dental hypersensitivity due to changes in hydrostatic pressure of the tooth. Thus, the present invention also includes a metal precipitating agent which may prevent unblocking of the intercrystalline spaces and increase the safety.

Catalase inhibiting compounds are also essential. These agents consist of about 0.05% to 5% of the formulation. Preferably from about 0.1 to 1% w/w. Catalase inhibiting compounds include compounds that release halogens such as such as alkali metal halogenated compounds such as sodium fluoride, sodium chloride etc. hydrofluoric acid, hydrochloric acid, potassium fluoride, cuprous fluoride, a tin fluoride such as stannous fluoride or stannous chlorofluoride, sodium fluorosilicate, ammonium fluorosilicate, sodium monofluorophosphate, alumina mono- and di-fluorophosphate. Other catalase inhibiting compounds include sulfides, aminoguanadine, hydroxylamine, hydroxylammonium chloride and reducing agents such as ascorbic acid, dithiothretrol. The preferred compounds are fluorine containing compounds because in addition to having anti-catalase activity, they also have a capability of precipitating metals which may destabilize peroxide. The most preferred halogenated compound is sodium fluoride within the range of about 0.05% to 1% w/w of the composition. In the present invention, sodium fluoride functions both as a metal precipitating compound and as a catalase inhibiting agent.

The following examples are further illustrative of the present invention, but it is understood that the invention is not limited thereto. All amounts and proportions referred to herein and in the appended claims are by weight unless otherwise indicated.

Gels were prepared as outlined in Table 1.

TABLE 1

| | % w/w | | | | | | | |
|---|---|---|---|---|---|---|---|---|
| Ingredient | Ex 1 | Ex 2 | Ex 3 | Ex 4 | Ex 5 | Ex 6 | Ex 7 | Ex 8 |
| Pluronic F127 | 30 | 30 | 30 | 30 | 30 | 30 | 30 | 30 |
| Water | 50 | 60 | 59.7 | 58.7 | 58.46 | 58.46 | 58.46 | 58.46 |
| Hydrogen Peroxide(30%) | 10 | 10 | 10 | 10 | 10 | 10 | 10 | 10 |
| Polyethylene glycol 600 | 10 | — | — | — | — | — | — | — |
| Sodium pyrophosphate | — | — | 0.3 | 0.3 | 0.3 | 0.3 | 0.3 | 0.3 |
| Dequest 2010 | — | — | — | 1.0 | 1.0 | 1.0 | 1.0 | 1.0 |
| Sodium Fluoride | — | — | — | — | 0.24 | — | 0.24 | 0.24 |
| Sodium Lauryl sulfate | — | — | — | — | — | 2.00 | — | 2.00 |
| Tween 20 | — | — | — | — | — | — | 2.00 | 2.00 |

The dental gels were prepared by adding sodium pyrophosphate and Dequest 2010 to distilled water until a clear solution was obtained. Sodium Lauryl sulfate and Tween 20 were then added to the mixture and stirring continued until the surfactants dissolved. Sodium fluoride was then added and nixing continued until a homogenous mixture was obtained. The resulting mixture was then transferred to a stainless steel premier vacuum mixture and pluronic F127 was added. The mixture was then mixed for 10 minutes without the vacuum after this period the vacuum was turned on and mixing carried out for an additional 30 minutes. Hydrogen peroxide was then added and mixing continued under vacuum for an additional 30 minutes. Prior to testing the pH of the gels was adjusted to 6.00 with sodium hydroxide.

The gels shown in Table 1 are described as ringing gels that have a rigid jelly like consistency which when placed in a container and the sides tapped lightly, the gels maintain their original configuration.

Tooth bleaching effectiveness of the above gels was determined by using extracted human teeth. The teeth were freshly extracted, freed of all adherent tissues and stored in a sterile saline solution. The teeth were removed and the color was measured using a chroma meter (Minolta CR221). Readings were taken in the L* a* and b* parameters. The teeth were then incubated in the various gels for an additional 30 minutes. After this period the gels were washed off and color was re-measured. The change in color (Delta E) was then calculated using the CIE L*a*b* color difference equation:

$$\text{Delta } E = [(\text{delta } L^*)^2 + (\text{delta } a^*)^2 + (\text{delta } b^*)^2]^{0.5}$$

The results are shown in Table 2.

TABLE 2

| Tooth # | Example | Delta E (increase in whiteness) |
|---|---|---|
| 1. | Commercial Product | 2.39 |
| 2. | Ex 1 | 3.36 |
| 3. | Ex 2 | 5.01 |
| 4. | Ex 3 | 5.00 |
| 5. | Ex 4 | 5.46 |
| 6. | Ex 5 | 5.98 |
| 7. | Ex 6 | 6.01 |
| 8. | Ex 7 | 7.10 |
| 9. | Ex 8 | 8.83 |

The table above shows the effect of humectant upon whitening effectiveness. Ex I contained the hydrocarbon humectant and Ex 2 lacked the humectant. Removal of the humectant increased the whitening effectiveness from Delta E of 3.36 to Delta E of 5.01. Addition of the pyrophosphate did not make a significant difference as shown in Ex 3. Formulations containing Sodium Pyrophosphate and Dequest 2010 (Ex 4) gave a further boost in whitening. Addition of the catalase inhibiting/metal precipitating agent also increased the whitening effectiveness as shown in Ex 5. The greatest effectiveness was obtained in Ex 8, a composition lacking a hydrocarbon humectant, containing a blend of chelating agents and a mixed surfactant system.

To evaluate the safety and efficacy of the tooth whitening compositions a clinical trial was performed. In this study, dental hypersensitivity was measured as a function of adverse effects upon enamel. Notably, hypersensitivity has been correlated with opening of dentinal tubules and enamel surface erosion. Eighteen subjects were selected to participate in this clinical trial; each cell consisted of three subjects. A maxillary impression was obtained for each subject and a vacuum formed custom tray or splint was fabricated for each subject.

Each subject placed the test gels in the custom tray and used the tooth-whitening product for approximately 6 hours/day. Tooth whitening was measured using the standard Vita (™) shade guide. Color measurements were performed at three days, five days and seven days of product usage. The results of the whitening efficacy are shown in Table 3. After the study the subjects were questioned with reference to dental hypersensitivity.

TABLE 3

Mean Color Improvement (Vita Tabs)

| Group | 3 days | 5 days | 7 days |
|---|---|---|---|
| Commercial Product | 2.8 | 4.2 | 5.0 |
| Ex 1 | 3.4 | 5.0 | 5.8 |
| Ex 2 | 4.3 | 5.5 | 6.3 |
| Ex 4 | 4.8 | 5.8 | 6.8 |
| Ex 5 | 5.2 | 6.2 | 7.3 |
| Ex 8 | 6.1 | 7.3 | 8.6 |

The results above show that in comparison to the commercial product sold under the trademark of Excel II, obtained from Discus Dental Inc, California which contains a hydrocarbon humectant, the formulation not containing the chelating agents (Ex 1) has a greater whitening effect showing that the hydrocarbon humectant reduces the whitening effectiveness. Ex 4 contains the solubilizing chelating agents and the data shows a further boost of whitening. The results also unexpectedly show that the addition of a precipitating chelating agent/catalase inhibiting agent (Ex 5) provides a further beneficial whitening effect. The greatest tooth whitening effect was obtained by composition (Ex 8) which contains surfactants that solubilize and emulsify chromogenic materials in addition to other ingredients detailed in table 1.

The data shows that the inventive composition discussed herein provide a substantially greater degree of tooth whitening in a shorter amount of time.

Safety of the formulations was determined by obtaining information concerning dental hypersensitivity after the clinical trial. The data are tabulated in Table 4 below:

TABLE 4

| Group | Percent Reporting Hypersensitivity |
|---|---|
| Commercial Product | 66% |
| Ex 1 | 66% |
| Ex 2 | 33% |
| Ex 4 | 100% |
| Ex 5 | 0% |
| Ex 6 | 0% |

The highest level of hypersensitivity was obtained in formulation lacking the metal precipitating agent/catalase inhibitor. The lowest level of was obtained with the composition containing the metal precipitating agent. Compositions containing humectants also showed increased hypersensitivity.

The relative rates of hypersensitivity reported in the published literature is consistent with those obtained in the present study.

A high concentration peroxide gel was then prepared to determine if tooth whitening can be rapidly performed in the dental office. The composition is shown in Table 5 below:

TABLE 5

| | % w/w | |
|---|---|---|
| Ingredient | Ex 1 | Ex 8 |
| Pluronic F127 | 30 | 30 |
| Water | 21 | 15.46 |
| Hydrogen peroxide (30%) | 49 | 49 |
| Sodium pyrophosphate | | 0.3 |
| Deguest 2010 | | 1.0 |
| Sodium Fluoride | | 0.24 |
| Sodium Lauryl sulfate | | 2.00 |
| Tween 20 | | 2.00 |

As in Table 1, the above formulations produced a non-relaxing or ringing gels. A clinical trial was performed using the above formulations as outlined below:

A cheek retractor was inserted into the patients mouth to keep the lips away from the teeth. Then cotton rolls were placed on the molars and the patients were asked to bite such that both the upper and lower teeth were visible. The shade of the teeth was then measured the Vita Shade guide. A thin layer of white petroleum jelly manufactured by Chesebrough-Ponds, Conn. was then was placed at the margins of the teeth and the gums. In accordance with this invention, any bioadhesive material which does not react with peroxide can be used instead to the white jelly.

The purpose of the petroleum jelly was to prevent the whitening gel from touching the gums. After placing the petroleum jelly, the whitening gel was placed on the facial surfaces of both the upper and lower teeth following the contours of the teeth and interproximal spaces and allowed to sit for one hour. After this period the retractors, petroleum jelly and gel and other materials were removed and the tooth color measured. The change in shade or improvement in tooth color is shown in Table 6.

TABLE 6

| | Initial Shade | Final Shade | Improvement in Shade |
|---|---|---|---|
| Ex 1 | A3 | A2 | 4 |
| Ex 2 | A3 | A1 | 7 |

The data shown above shows that significant improvement can be obtained in one hour of treatment time using a higher concentration of peroxide in the inventive composition. In addition, at the end of the clinical study, unlike relaxing gels, the ringing gel did not flow and stayed in place. Neither subjects reported hypersensitivity.

Collectively, the present inventive compositions show a substantial improvement over prior art because they have significantly greater tooth whitening effect and have significantly reduced levels of dental hypersensitivity.

What is claimed is:

1. A method of whitening teeth, said method comprising the steps of:
    applying a bioadhesive material to the gums;
    applying a tooth whitening hydrogel composition to a surface of the teeth wherein the tooth whitening composition includes:
        a peroxide compound in the range of about 1% to about 30% by weight;
        a mixed metal chelating system in an amount in the range of about 0.1% to about 8% by weight, wherein the metal chelating system includes a condensed pyrophosphate, an organic phosphate chelating agent, and a metal precipitating agent;

a catalase inhibitor; and with a proviso that the tooth whitening composition does not contain a hydrocarbon humectant;

contacting the tooth whitening hydrogel composition on the surface of the teeth with a flexible film, wherein the flexible film does not react with the bioadhesive material and does not react with the peroxide compound; and molding the flexible film to cover the surfaces of the teeth to prevent contact between the tooth whitening composition and soft tissues of the mouth.

2. The method of claim 1, wherein the condensed pyrophosphate is a compound selected from the group consisting of sodium pyrophosphate, sodium triphosphate, trisodium phosphate and combinations thereof, and wherein the condensed pyrophosphate has a concentration in the range of about 0.25 wt % to about 2 wt % of the total composition.

3. The method of claim 1, wherein the organic phosphate chelating agent is 1-hydroxyethylidene-1,1-diphosphonic acid and has a concentration in the range of about 0.25 wt % to about 2 wt % of the total composition.

4. The method of claim 1, wherein the metal precipitating agent is a fluoride compound.

5. The method of claim 1, wherein the fluoride compound has a concentration in the range of about 0.1 wt % to about 1 wt % of the total composition.

6. The method of claim 1, wherein the catalase inhibitor has a concentration in the range of about 0.1 wt % to about 2 wt % of the total composition.

7. The method of claim 1, wherein the tooth whitening composition further includes a thickening agent.

8. The method of claim 7, wherein the thickening agent is a polyoxyethylene-polyoxypropylene block copolymer having a concentration in the range of about 15 wt % to about 50 wt % of the total composition.

9. A method of whitening teeth, said method comprising the step of:

applying a bioadhesive material to the gums;

contacting at least one tooth surface with an oral care hydrogel composition, wherein the oral care composition includes:

a peroxide compound in the range of about 1% to about 30% by weight;

a mixed metal chelating system in an amount in the range of about 0.1% to about 8.0% by weight, wherein the metal chelating system includes a condensed pyrophosphate, an organic phosphate chelating agent, and a metal precipitating agent;

a catalase inhibitor; and with a proviso that the oral care hydrogel composition does not contain a hydrocarbon humectant.

10. The method of claim 9, further comprising the step of: contacting the oral care composition on the tooth surface with a dental device.

11. The method of claim 10, where the dental device is selected from the group consisting of a tooth brush, a dental strip, a dental tray, and a dental splint.

12. The method of claim 9, wherein the oral care composition is a gel and is contacted with the tooth surface for a time period of about one hour.

13. The method of claim 9, wherein the catalase inhibitor has a concentration in the range of about 0.1 wt % to about 2 wt % of the total composition.

14. The method of claim 9, wherein the oral care composition further includes a thickening agent.

15. The method of claim 14, wherein the thickening agent is a polyoxyethylene-polyoxypropylene block copolymer having a concentration in the range of about 15 wt % to about 50 wt % of the total composition.

* * * * *